United States Patent
Ehrismann (10) Patent No.: US 7,632,385 B2
(45) Date of Patent: Dec. 15, 2009

(54) REFERENCE ELECTRODE FOR POTENTIOMETRIC MEASUREMENTS, AND METHOD OF MONITORING THE REFERENCE ELECTRODE

(75) Inventor: Philippe Ehrismann, Uster (CH)

(73) Assignee: Mettler-Toledo AG, Greifensee (CH)

( * ) Notice: Subject to any disclaimer, the term of this patent is extended or adjusted under 35 U.S.C. 154(b) by 868 days.

(21) Appl. No.: 11/162,872

(22) Filed: Sep. 27, 2005

(65) Prior Publication Data

US 2006/0070889 A1     Apr. 6, 2006

(30) Foreign Application Priority Data

Oct. 4, 2004    (EP) .................... 04104850

(51) Int. Cl.
*G01N 27/26*    (2006.01)
(52) U.S. Cl. ............. 204/435; 204/433; 205/787.5; 73/304 R; 73/290 R; 73/313
(58) Field of Classification Search ............. 204/433, 204/435; 73/291–334; 205/787.5
See application file for complete search history.

(56) References Cited

U.S. PATENT DOCUMENTS

| 4,284,343 A | * | 8/1981 | Junghanns .............. 396/606 |
| 4,360,415 A | | 11/1982 | Brezinski |
| 5,070,346 A | * | 12/1991 | Mochizuki et al. ............. 347/7 |
| 6,495,012 B1 | * | 12/2002 | Fletcher et al. ............. 204/435 |
| 6,894,502 B2 | | 5/2005 | Feng |
| 2003/0150726 A1 | * | 8/2003 | West et al. .................. 204/433 |

FOREIGN PATENT DOCUMENTS

| DE | 35 13 751 C1 | 3/1986 |
| DE | 37 02 501 A1 | 8/1987 |
| DE | 196 39 372 A1 | 4/1998 |
| GB | 2 370 646 A | 7/2002 |

* cited by examiner

*Primary Examiner*—Nam X Nguyen
*Assistant Examiner*—Bach T Dinh
(74) *Attorney, Agent, or Firm*—Standley Law Group LLP (57) ABSTRACT

A reference electrode for potentiometric measurements has a housing (2) with a hollow space (4) containing a liquid reference electrolyte (6) as well as a conductor element (8) immersed in the reference electrolyte. In addition, the housing has a diaphragm (12) through which the reference electrolyte can be brought into contact with a measuring medium (10) outside of the housing. Furthermore, means are provided to effect an outflow of the reference electrolyte through the diaphragm. A first electrical contact element (20, 36) is arranged in the hollow space in such a manner that the contact element is immersed in the reference electrolyte as long as the fill level (18) of the reference electrolyte does not fall below a threshold value ($F_S$), and that the contact element is not immersed in the reference electrolyte if the fill level falls short of the threshold value.

16 Claims, 5 Drawing Sheets

REFERENCE ELECTRODE FOR POTENTIOMETRIC MEASUREMENTS, AND METHOD OF MONITORING THE REFERENCE ELECTRODE

TECHNICAL FIELD

The invention relates to a reference electrode for potentiometric measurements as well as a method of monitoring the reference electrode.

THE STATE OF THE ART

Numerous electrochemical sensors are known which require a reference electrode with a stable electrical potential in order to function properly. A widely used type of reference electrodes is equipped with a diaphragm of a porous material through which a reference electrolyte which is contained in the reference electrode and is present in liquid form can be brought into contact with a measuring medium. A reference electrode meeting this generic description is presented in published German patent application 100 53 979 A1 as a part of an electrochemical measuring chain.

Particularly when reference electrodes are used in monitoring and/or controlling a chemical or microbiological process, the measuring medium can contaminate the diaphragm or penetrate into the reference electrolyte so as to dilute or contaminate the reference electrolyte. The result in either case can be an uncontrollable change in the voltage potential set by the reference electrolyte and thus a corruption of the measured values. A known way of avoiding such undesirable effects is to put the reference electrolyte under an increased pressure in relation to the measuring medium, whereby the reference electrolyte is slowly but steadily pushed through the diaphragm into the measuring medium. This prevents the measuring medium from penetrating the reference electrode and in addition provides for a continuous flushing of the diaphragm, which works against the accumulation of contaminating deposits from the measuring medium. It will however be necessary to replace the outflow of reference electrolyte either continuously or at discrete time intervals.

The reference electrodes of the known state of the art suffer from the drawback that the fill level of the reference electrolyte is difficult or in some cases even impossible to monitor. While it is possible to visually determine the fill level in reference electrodes with glass housings, this can involve a considerable expenditure of time and attention, particularly in process systems that operate continuously and/or contain several reference electrodes. Furthermore, the interior of the reference electrode is in many cases not accessible for direct inspection, for example if the reference electrode is installed in an armature or if it is immersed in a turbid measuring medium.

SUMMARY OF THE INVENTION

The objective of the invention is to propose an improved reference electrode as well as a method of monitoring the reference electrode, specifically in order to avoid the aforementioned drawbacks.

These objectives are attained with the reference electrode defined in the appended claims, as well as the method claimed there.

The reference electrode according to the invention comprises a housing of electrically insulating material, wherein the housing has at least one hollow space containing a liquid reference electrolyte as well as a conductor element immersed in the reference electrolyte. In addition, the housing has at least one diaphragm which is permeable for the reference electrolyte and through which the reference electrolyte can be brought into contact with a measuring medium outside of the housing. Furthermore, there are means to effect an outflow of the reference electrolyte through the diaphragm. A first electrical contact element is arranged in the hollow space in such a manner that the contact element is immersed in the reference electrolyte as long as the fill level of the reference electrolyte does not fall below a threshold value, and that the contact element is not immersed in the reference electrolyte if the fill level of the reference electrolyte falls below the threshold value. As the reference electrolyte necessarily has a good electrical conductivity, there will be a lower electrical resistance between the first contact element and the conductor element if the contact element as well as the conductor element is immersed in the reference electrolyte. This situation is present if the fill level of the reference electrolyte is high enough. Else, i.e., if the fill level is too low, the reference electrolyte forms no electrical connection between the contact element and the conductor element, so that the electrical resistance between them is significantly higher than with a sufficient fill level.

Consequently, under the inventive monitoring method, the electrical resistance that is present between the first contact element and the conductor element is monitored in regard to whether or not it exceeds a predefined first threshold resistance. The first threshold resistance needs to be selected so that it lies between the resistance values that are measured, respectively, in a full reference electrode and in an insufficiently filled reference electrode. As a rule, these resistance values differ from each other to a quite significant degree, so that a suitable threshold resistance can be found without difficulty.

Advantageous further embodiments of the invention are defined in the dependent claims.

There are several possibilities to achieve the outflow of reference electrolyte through the diaphragm which is necessary to keep the diaphragm clean and to avoid contamination of the reference electrolyte by the measuring medium. Specifically, the outflow can be generated by using the effect of gravity, if the fluid level of the reference electrolyte lies higher than the fluid level of the measuring medium. In one embodiment, the reference electrolyte is put under an elevated pressure in relation to the measuring solution, for example an overpressure of 0.2 to 0.5 bar.

It meets the purpose and is sufficient for many applications to provide a first contact element in the form of a section of wire or a strip of metal which reaches from the upper part of the reference electrode into a mid-range of the hollow space located below. In contrast to this, the first contact element in one embodiment is configured ring-shaped around a longitudinal axis of the housing. This is particularly advantageous in cases where the reference electrode is installed in a slanted position, as is often the case with reference electrodes installed in reactors. As a result of the ring-shaped configuration of the first contact element, the reference electrode can be arranged in an arbitrarily rotated position relative to the longitudinal axis, with no influence on the distance between the lower end of the first contact element and the fill level of the reference electrolyte. It is practical to arrange the first contact element in one embodiment on the inside of a housing wall that delimits the hollow space, for example on the inside of a cylindrical housing wall which contains the reference electrolyte. According to another embodiment, the first contact element is formed advantageously by an electrically conductive coating, which permits a very compact design of the reference electrode.

In principle, the reference electrode can be configured as an individual assembly with its own housing. A compact and user-friendly configuration is defined in some embodiments, according to which the reference electrode is arranged in a single-rod measuring chain, with the reference electrode preferably arranged concentrically around a measuring electrode.

In one configuration, a second electrical contact element is arranged in the hollow space of the reference electrode in such a way that the second electrical contact element is not immersed in the reference electrolyte as long as the fill level of the latter does not exceed a maximum value, and that the second electrical contact element is immersed in the reference electrolyte if its fill level exceeds the maximum value. Specifically, the foregoing concept makes it possible to perform the version of the monitoring method that is defined by one embodiment, wherein an electrical resistance that is present between the second contact element and the conductor element is monitored in regard to whether or not it is below a second threshold resistance.

In an exemplary embodiment of the method, warning signals and/or control signals are generated when the monitored resistance exceeds the first threshold resistance and, if applicable, when the monitored resistance falls below the second threshold resistance. The warning signals can serve to alert the user that the reference electrolyte needs to be replenished and, if applicable, that the maximum fill level has been reached and the replenishment process has thus been completed. However, it is also possible in the case of an automated operation to use the control signal to initiate a replenishment process in which reference electrolyte is added to the reference electrode and the replenishment process is terminated when the maximum fill level has been attained.

BRIEF DESCRIPTION OF THE DRAWINGS

Embodiments of the invention are hereinafter described in more detail with references to the drawings, wherein.

DETAILED DESCRIPTION OF A PREFERRED EMBODIMENT

Figure 1:
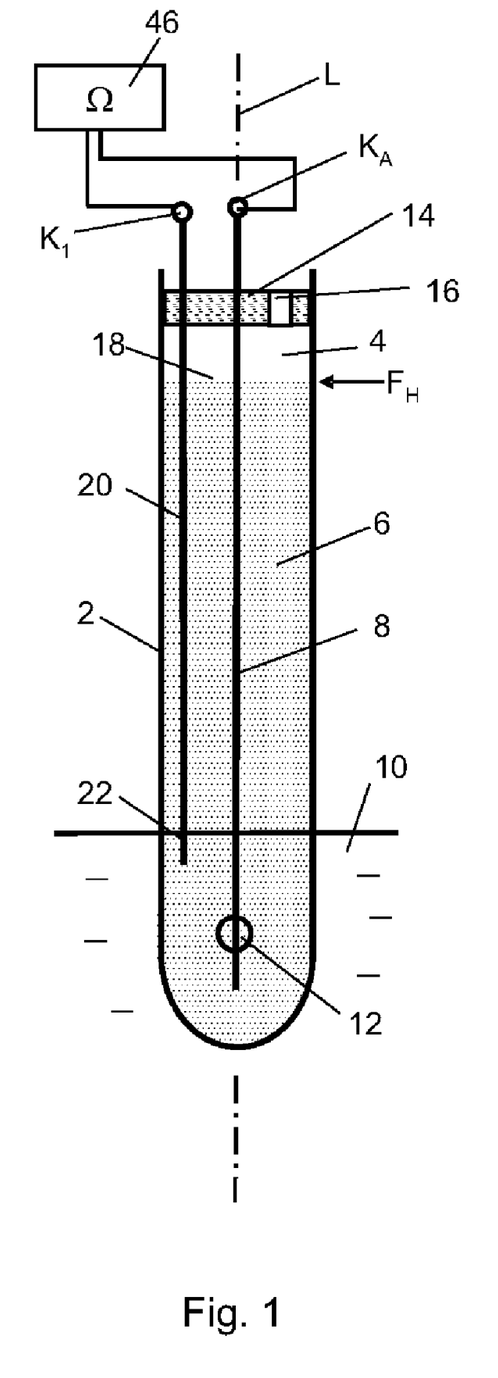
FIG. 1 represents a lengthwise central cross-section of a reference electrode in the filled condition.
Figure 2:
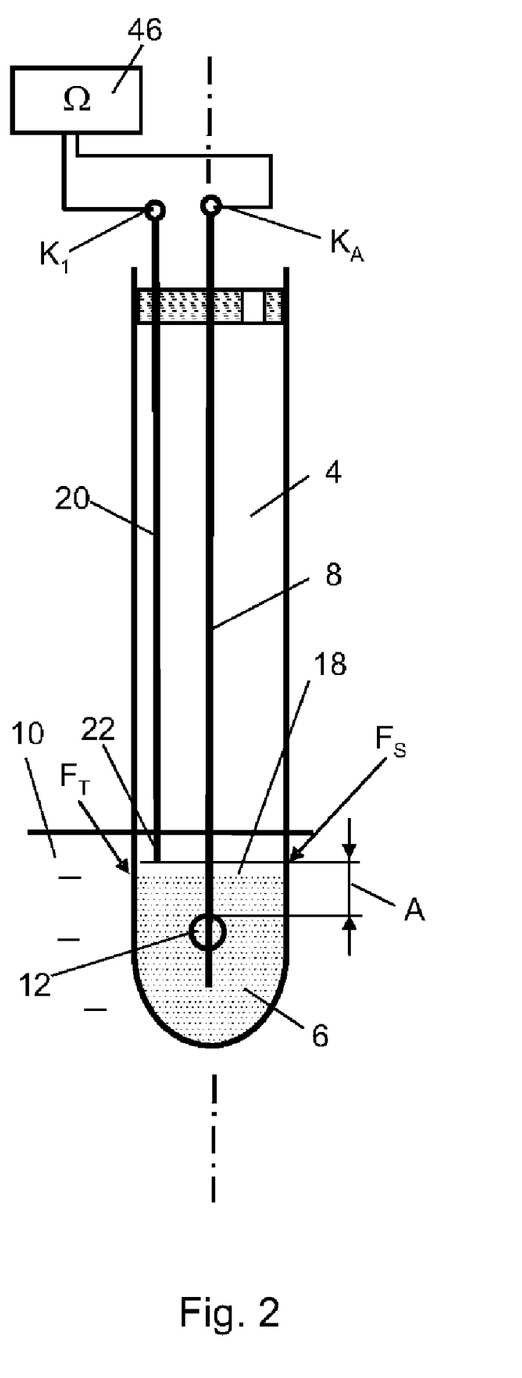
FIG. 2 represents a lengthwise central cross-section of the reference electrode of FIG. 1, with the fill level of the reference electrode lying below the threshold value.

The reference electrode shown in FIGS. 1 and 2 has a glass housing 2 with an interior hollow space 4 containing a liquid reference electrolyte 6 as well as a conductor element 8 that is immersed in the reference electrolyte 6. In the illustrated operating position, the longitudinal axis L of the reference electrode is aligned substantially in the vertical direction, and its bottom portion is immersed in a measuring medium 10. The housing 2 further has a diaphragm 12 that is arranged in the bottom portion of the reference electrode and is permeable for the reference electrolyte, allowing the reference electrolyte 6 to be in contact with the measuring medium 10 that is present outside of the housing. The reference electrode can for example be an Ag/AgCl electrode of a kind that is known per se, where the conductor element 8 is a silver wire that is coated with silver chloride and the reference electrolyte 6 is for example a 3-molar aqueous solution of potassium chloride. The diaphragm 12 is formed for example of a plug of a porous ceramic material.

The reference electrode further includes a top closure element 14 with a sealed passage for the conductor element 8. The top closure element 14 further has an opening 16 that is provided on the one hand for the replenishment of electrolyte but on the other hand also allows the hollow space 4 to be put under pressure. The hollow space 4 and the reference electrolyte 6 contained in it can for example be put under an overpressure of 0.2 to 0.5 bar, which has the effect of pushing the reference electrolyte 6 slowly but continuously through the diaphragm 12 into the measuring medium 10. As a result, a contamination of the diaphragm 12 and an undesirable penetration of measuring medium 10 into the reference electrolyte are prevented.

However, the continuous outflow of reference electrolyte 6 has the consequence that its fluid level 18 will gradually decrease and, for example, go down from an initially high fill level $F_H$ as shown in FIG. 1 to a low fill level $F_T$ as shown in FIG. 2. It is immediately clear that a further descent of the electrolyte level 18 down to the diaphragm 12 is undesirable, as this would lead to a decrease and finally to a total absence of the desired outflow of reference electrolyte 6. As a means to avoid this situation, a first electrical contact element 20 which allows the fill level to be monitored is arranged in the hollow space 4.

Like the conductor element 8, the first contact element runs through a sealed passage in the top closure element 14 and reaches inside the hollow space 4. The first contact element 20 is dimensioned and arranged in such a way that its lower end 22 is located higher than the upper edge of the diaphragm 12 by a distance A. As can be concluded from FIG. 1, when the reference electrode is filled sufficiently, the first contact element 20 is immersed in the reference electrolyte 6. This stands in contrast to the situation shown in FIG. 2, where the electrolyte level 18 has sunk to a fill level $F_T$ that is below the bottom end 22 of the first contact element 20, so that the latter is not immersed in the reference electrolyte 6. Accordingly, the height at which the lower end 22 is located in reference to the electrode housing defines a threshold value $F_S$ for the fill level of the reference electrolyte 6. As long as the fill level does not fall below the threshold value $F_S$, the first contact element 20 is immersed in the reference electrolyte 6; if the fill level falls below the threshold $F_S$, the first contact element 20 is no longer immersed in the reference electrolyte 6.

By measuring the electrical resistance between the conductor element 8 and the first contact element 20, it can be determined directly whether or not the first contact element 20 is immersed in the reference electrolyte 6. As a practical matter, this is accomplished by measuring the resistance $R_1$ between an outside contact terminal $K_A$ of the conductor element and an outside contact terminal $K_1$ of the first contact element 20. When the first contact element 20 is immersed, this resistance is comparatively small, typically less than 100 kΩ, due to the good electrical conductivity of the reference electrolyte 6. In contrast, when the first contact element 20 is not immersed, the resistance $R_1$ is significantly higher, typically more than 1000 kΩ, or even more. Consequently, the decrease of the fill level below the threshold value $F_S$ manifests itself through an increase in the resistance $R_1$ by a power of 10 or more.

Figure 3:
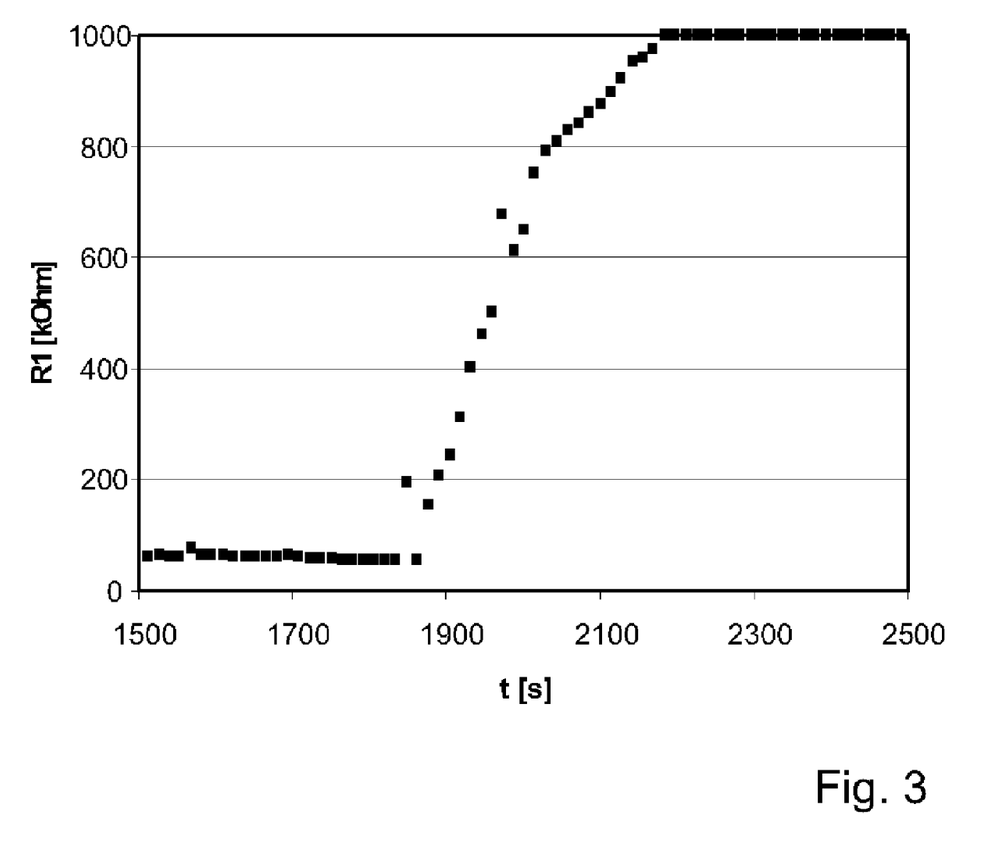
FIG. 3 represents a graph of the time profile of the electrical resistance between the first electrical contact element and the conductor element of the reference electrode of FIGS. 1 and 2.

An example of how the aforementioned electrical resistance $R_1$ changes as a function of the time t is illustrated in FIG. 3. Initially, i.e., up to a time of about 1800 seconds, the resistance $R_1$ is substantially constant and has a value, in a round number, of 60 kΩ. At a time of around 1900 seconds, $R_1$ rises abruptly, i.e., within about 100 seconds, to values above 1000 kΩ. The range of the measuring instrument that was used in this case had an upper limit of 1000 kΩ, which was strongly exceeded at a time of 2100 seconds. In the practical application, the resistance $R_1$ is monitored by means of an appropriate monitoring device 46 (see FIGS. 1, 2 and 4-6) against the criterion of exceeding a predefined, preferably adjustable first threshold resistance $R_{1S}$, which needs to be selected so that it lies between the resistance values that are measured, respectively, when the reference electrode is full and when it is not sufficiently filled. As an example, the first threshold resistance $R_{1S}$ is set to a value of 400 kΩ.

As a practical measure, a warning signal is triggered when the first threshold resistance $R_{1S}$ is exceeded. For example, an optical and/or acoustical signal device can be provided for this purpose. This can be used to alert the user that reference electrolyte needs to be replenished, or that the reference electrode needs to be replaced. It is also possible when the threshold resistance $R_{1S}$ is exceeded to generate a command signal that is sent to a replenishing device where it triggers a replenishing process. For example, the replenishing device can be programmed in such a way that it injects a predetermined quantity of reference electrolyte into the reference electrode when a command signal is received.

As can easily be concluded from FIGS. 1 and 2, the distance A represents a safety reserve insofar as when the electrolyte level 18 falls below the threshold $F_S$, it is initially still above the diaphragm 12, so that a certain reserve operating period remains before it becomes absolutely mandatory to replenish the reference electrolyte 6. In order to provide an adequate warning period, it is practical to select a larger distance A the faster the outflow rate of the reference electrolyte 6.

Figure 4:
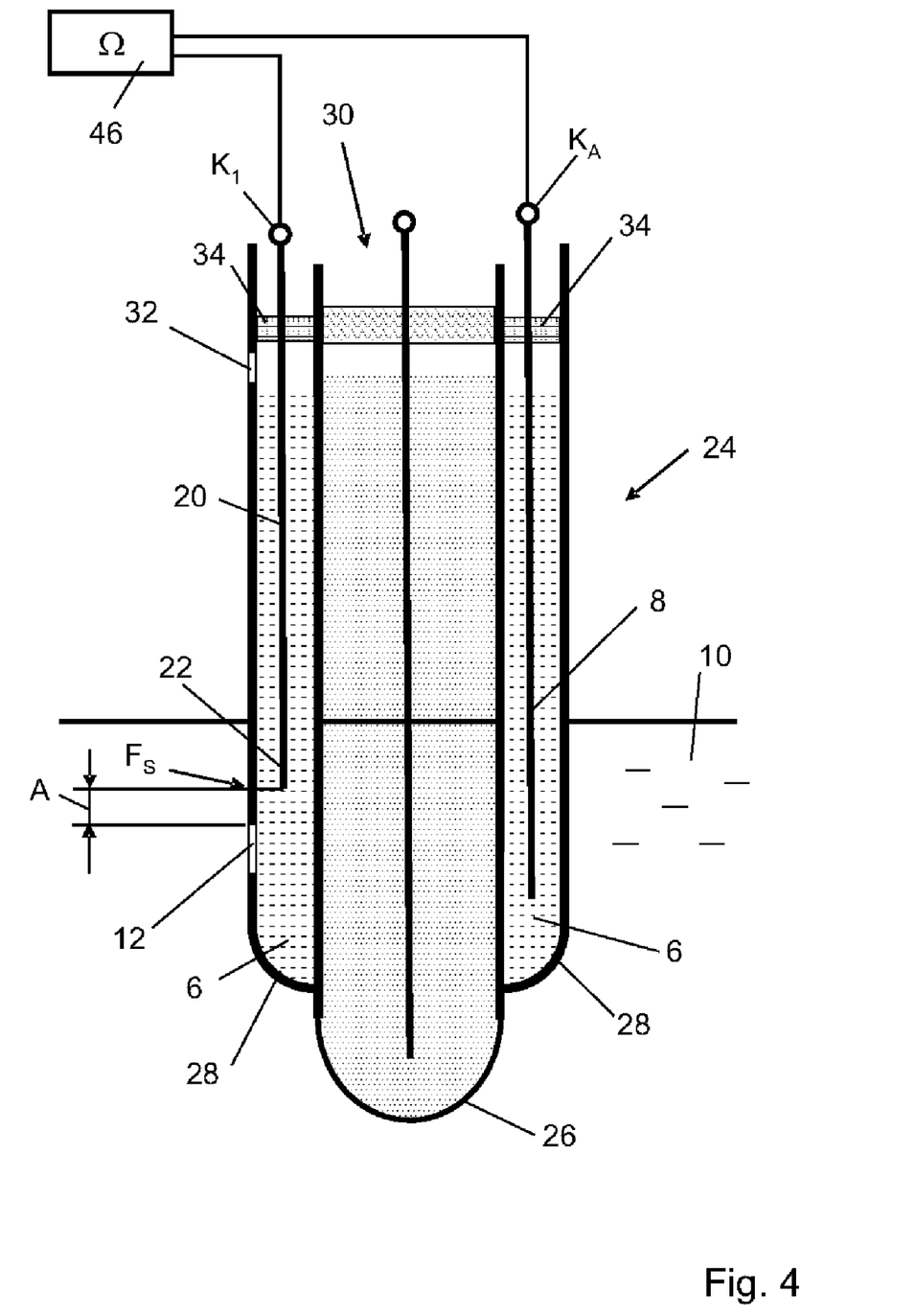
FIG. 4 represents a lengthwise central cross-section of a single-rod measuring chain in the filled condition.

FIG. 4 shows a further reference electrode which is integrated in a measuring probe that is configured as a single-rod measuring chain. The measuring probe has a probe housing 24 made of glass or plastic, whose bottom end is immersed in the measuring medium 10. The probe housing 24 includes a central chamber 26 as well as a ring chamber 28 arranged concentrically around the central chamber 26. The central chamber 26 contains a first half-cell element 30 configured as a pH-electrode, while a second half-cell element configured as reference electrode is accommodated in the ring chamber 28. The principal design structure of the two half-cell elements is known per se and will not be explained in detail here. In place of a pH-electrode, the measuring probe can contain another half-cell element such as for example a redox electrode.

The ring chamber 28 has a diaphragm 12 in the immersion area, and in its uppermost portion it is additionally equipped with a lateral refill opening 32. The ring chamber 28 further contains a reference electrolyte solution 6, for example a saturated solution of potassium chloride, in which a silver wire coated with a silver chloride layer is immersed, functioning as a conductor element 8. The latter is routed in a sealed passage through a top closure part 34 of the ring chamber 28 to an outside contact terminal $K_4$.

The reference electrode of FIG. 4 further includes a first electrical contact element 20 which is likewise routed in a sealed passage through the top closure part 34 and reaches into the ring chamber 28. The first contact element 20 is dimensioned and arranged so that its bottom end 22 lies higher by a distance A than the upper edge of the diaphragm 12. The first contact element 20 is further equipped with an outside contact terminal $K_1$. As in the design configuration of FIGS. 1 and 2 discussed above, the arrangement of the first contact element 20 permits the fill level of the reference electrolyte 6 to be monitored. In regard to the monitoring function, the interior space of the ring chamber 28 is functionally equivalent to the interior hollow space 4 of the reference electrode of FIGS. 1 and 2.

Figure 5:
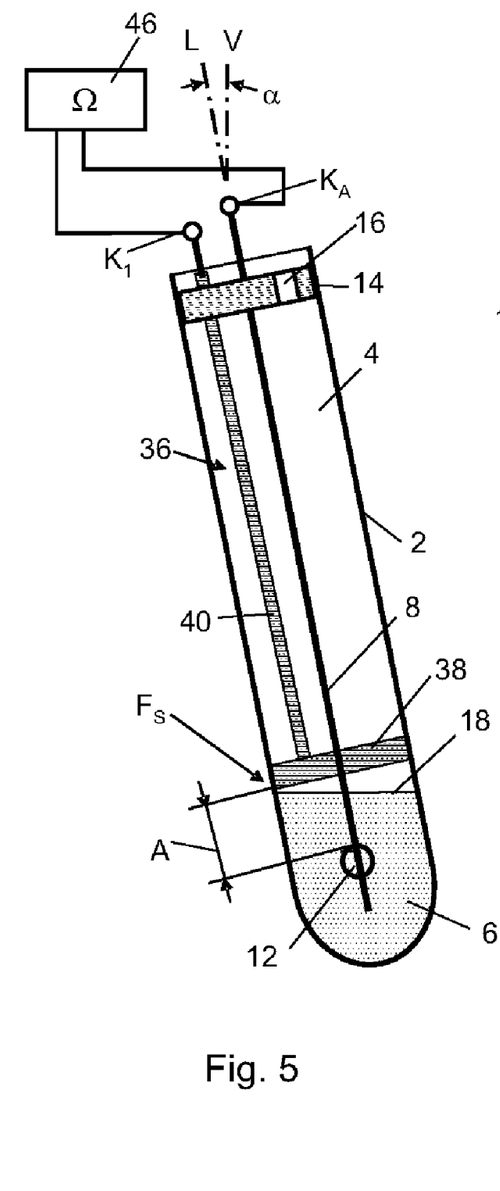
FIG. 5 represents a lengthwise central cross-section of a further reference electrode that is installed in a slanted position.
Figure 6:
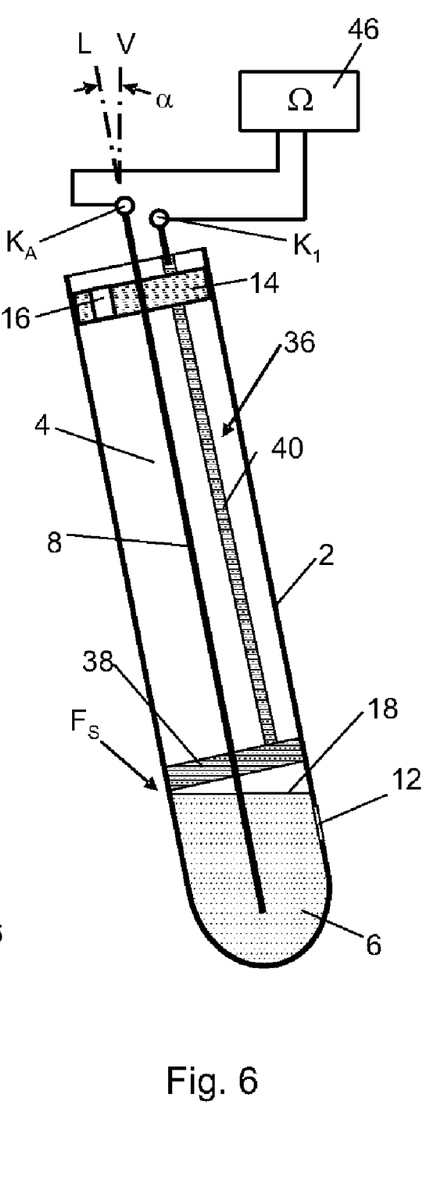
FIG. 6 represents a lengthwise central cross-section of the same reference electrode as shown in FIG. 5, except that its position has been rotated by 90°.

FIGS. 5 and 6 illustrate a further reference electrode which is distinguished from the reference electrode in FIGS. 1 and 2 only by the design of the first electrical contact element. Accordingly, components that occur identically in FIGS. 1 and 2 as well as 5 and 6 are identified by the same reference symbols and are not described in detail here. The first contact element 36 has an electrically conductive ring band 38 arranged on the inside of the housing 2, with the plane of the ring extending substantially perpendicular to the longitudinal axis L of the housing 2. A distance A is provided between the lower edge of the first contact element 36 and the upper edge of the diaphragm 12. An electrically conductive lengthwise strip 40 runs on the inside of the housing 2 from the ring band 38 to the upper end of the housing 2, where the strip 40 has an outside terminal $K_1$. It is advantageous if the ring band 38 and lengthwise strip 40 are designed as conductor tracks which are layered onto the inside wall of the housing. In the illustrated example, the lengthwise strip 40 runs between the inside wall of the housing and the outside edge of the top closure element 14, whereby a fluid-tight passage is created.

As can be concluded from looking at FIGS. 5 and 6 together, the ring-shaped design of the first contact element 36 is particularly advantageous if the reference electrode is installed in an oblique, i.e., non-vertical, position. Oblique mounting positions are used frequently in practice and are for example dictated as a given condition with many reaction vessels. Different from a first contact element configured as a longitudinal wire or a longitudinal strip, the ring band 38 has a shortest distance to the fluid level 18 of the reference electrolyte 6 that is independent of the rotary position of the housing 2 relative to its longitudinal axis L.

Accordingly, as the reference electrolyte flows out during operation of the reference electrode, the threshold level $F_S$ of the fill condition where the contact between the first contact element 36 and the reference electrolyte 6 is interrupted is always the same regardless of the rotary position. Thus, it is not necessary to take the prospective rotary position of the reference electrode into account when applying the first contact element 36, as the rotary position can be changed even later without harmful consequences for the monitoring of the fill level position.

However, as can likewise be concluded from FIGS. 5 and 6, depending on the rotary position, the diaphragm 12 takes on different height positions in relation to the fluid level 18. For example in the first rotary position according to FIG. 5, the diaphragm is still clearly below the fluid level 18, while in the 90°-rotated position according to FIG. 6, the fluid level 18 lies only slightly above the diaphragm 12. This effect needs to be taken into account in the initial determination of the distance A between the lower edge of the ring band 38 and the upper edge of the diaphragm 12.

If one first considers the limiting case where the electrical contact between the first contact element 36 and the reference electrolyte 6 is to be interrupted exactly at the time when the fluid level 18 has sunk to the upper edge of the diaphragm 12, the distance A should be selected as follows, in the case where the housing 2 is shaped as a circular cylinder:

$$A = D \tan \alpha$$

wherein D stands for the inside diameter of the housing 2 and α for the angle at which the longitudinal axis L is inclined relative to the vertical V. For a vertical installation, the required distance A is equal to zero, which represents the limiting case under consideration here. With increasing angle of inclination α (in view of the function of the reference electrode, the angle α must be less than 90°) the required distance A increases.

As a rule, however, in order to obtain an adequate warning time period, one will choose a larger distance A' for which a practical selection would be as follows:

$$A' = A_0 + D \tan \alpha$$

wherein $A_0$ represents a constant. For housings that are not in the shape of a circular cylinder, one will have to go through analogous geometrical considerations of a commensurately more complex character.

The first ring-shaped contact element 36 which is explained here for an individual reference electrode can be used analogously in single-rod measuring chains, especially when the latter are intended for installation in an inclined position.

Figure 7:
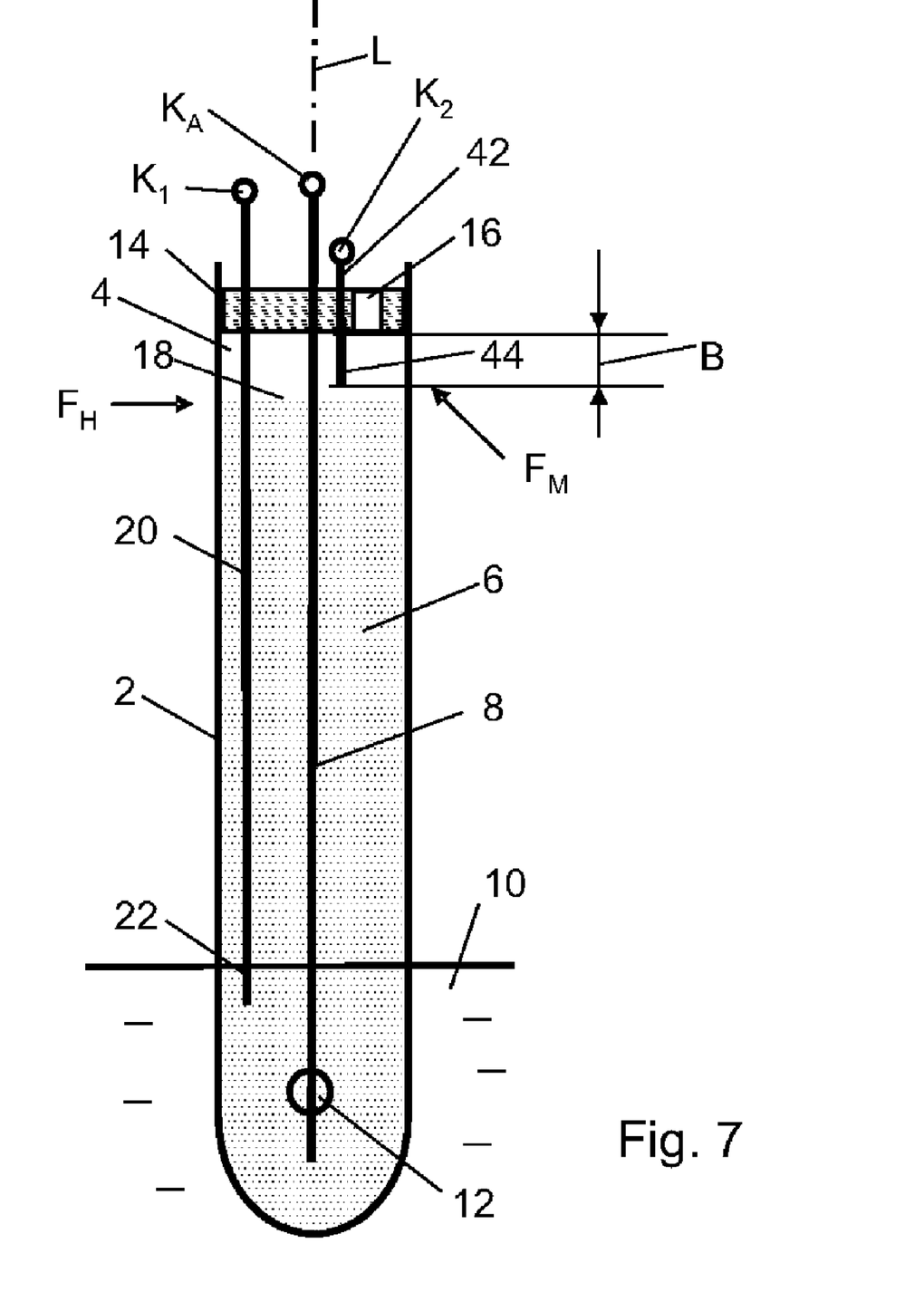
FIG. 7 represents a lengthwise central cross-section of a further reference electrode that is close to the maximally filled condition.

The reference electrode illustrated in FIG. 7 is configured like the reference electrode of FIGS. 1 and 2, but contains in addition a second electrical contact element 42 which is likewise routed in a sealed arrangement through the top closure element 14 and reaches into the hollow space 4. The second contact element 42 is dimensioned and arranged so that its lower end 44 is located at a distance B below the underside of the upper closure 14. At the fill level shown in FIG. 7, the second contact element 42 is not immersed in the reference electrolyte 6. The height position of the bottom end 44 of the second contact element 42 in relation to the electrode housing defines a threshold level $F_M$ for the fill level of the reference electrolyte 6. As long as the fill level does not exceed the threshold level $F_M$, the second contact element 42 is not immersed in the reference electrolyte 6; if however the fill level exceeds the maximum level $F_M$, then the second contact element 42 is immersed in the reference electrolyte 6.

By measuring the electrical resistance between the conductor element 8 and the second contact element 42, one can determine directly whether or not the second contact element 42 is immersed in the reference electrolyte. As a practical way of making this determination, one measures the resistance $R_2$ between an outside contact terminal $K_A$ of the conductor element 8 and an outside contact terminal $K_2$ of the second contact element 42. As explained already in the context of the first contact element 22, the value of the electrical resistance $R_2$ likewise depends to a significant extent on whether or not the second contact element 42 is immersed in the reference electrolyte 6. An increase of the fill level above the maximum value $F_M$, in particular, manifests itself in a significant decrease of the resistance $R_2$, for example from over 1000 kΩ to fewer than 100 kΩ. As a practical measure, a warning signal is triggered when the resistance $R_2$ falls below the second threshold resistance $R_{2S}$. For example, an optical and/or acoustical signal device can be provided for this purpose. This can be used to alert the user that the replenishing of reference electrolyte needs to be terminated. It is also possible when the resistance $R_2$ falls below the second threshold resistance $R_{2S}$ to generate a command signal that is sent to a replenishing device where it stops a currently running replenishing cycle.

The second contact element 42 which is explained here with reference to FIG. 7 can also be used analogously in the reference electrodes illustrated in FIGS. 1 and 2 as well as in FIGS. 4 and 5.

What is claimed is:

1. A reference electrode for potentiometric measurements, comprising:
   a housing of electrically insulating material, having at least one hollow space with a liquid reference electrolyte contained therein, up to a fill level;
   a conductor element immersed in the reference electrolyte;
   at least one diaphragm in the housing, the diaphragm being permeable for the reference electrolyte so that the reference electrolyte can be brought into contact with a measuring medium outside of the housing;
   means for effecting outflow of the reference electrolyte through the diaphragm; and
   a first electrical contact element, arranged in the hollow space such that the first contact element is immersed in the reference electrolyte as long as the fill level is above a threshold value and that the first contact element is not in contact when the fill level is below the threshold value,
   wherein a monitoring device cooperates with the reference electrode to measure an electrical resistance between the conductor element and the first electrical contact element.

2. The reference electrode of claim 1, wherein:
   the reference electrolyte is put under an elevated pressure relative to the measuring medium.

3. The reference electrode of claim 2, wherein:
   the first contact element is configured in the shape of a ring around a longitudinal axis of the housing.

4. The reference electrode of claim 1, wherein:
   the first contact element is configured in the shape of a ring around a longitudinal axis of the housing.

5. The reference electrode of claim 3, wherein:
   the first contact element is arranged on the inside of a housing wall which delimits the hollow space.

6. The reference electrode of claim 1, wherein:
   the first contact element is arranged on the inside of a housing wall which delimits the hollow space.

7. The reference electrode of claim 5, wherein:
   the first contact element is formed by an electrically conductive coating.

8. The reference electrode of claim 1, wherein:
   the first contact element is formed by an electrically conductive coating.

9. The reference electrode of claim 7, wherein:
   the reference electrode is arranged in a single-rod measuring chain, preferably concentric around a measuring electrode.

10. The reference electrode of claim 1, wherein:
    the reference electrode is arranged in a single-rod measuring chain, preferably concentric around a measuring electrode.

11. The reference electrode of claim 9, further comprising:
    a second electrical contact element, arranged inside the hollow space such that the second electrical contact element is immersed in the reference electrolyte only when the reference electrolyte fill level exceeds a maximum value.

12. The reference electrode of claim 1, further comprising:
a second electrical contact element, arranged inside the hollow space such that the second electrical contact element is immersed in the reference electrolyte only when the reference electrolyte fill level exceeds maximum value.

13. A method of monitoring a reference electrode, comprising the steps of:
providing the reference electrode, the reference electrode comprising a housing of electrically insulating material, having at least one hollow space with a liquid reference electrolyte contained therein, up to a fill level, a conductor element immersed in the reference electrolyte, at least one diaphragm in the housing, the diaphragm being permeable for the reference electrolyte so that the reference electrolyte can be brought into contact with a measuring medium outside of the housing, means for effecting outflow of the reference electrolyte through the diaphragm, and a first electrical contact element, arranged in the hollow space such that the first contact element is immersed in the reference electrolyte as long as the fill level is above a threshold value and that the first contact element is not in contact when the fill level is below the threshold value; and
monitoring a first electrical resistance between the first contact element and the conductor element with regard to the first electrical resistance exceeding a first threshold resistance.

14. The method of claim 13, wherein the reference electrode further comprises a second electrical contact element and the method comprises the further step of:
monitoring a second electrical resistance between the second contact element and the conductor element with regard to the second electrical resistance falling below a second threshold resistance.

15. The method of claim 13, further comprising the step of:
generating at least one of a warning signal and a command signal when the first threshold resistance is exceeded.

16. The method of claim 14, further comprising the step of:
generating at least one of a warning signal and a command signal when either the first threshold resistance is exceeded or there is a shortfall below the second threshold resistance.

\* \* \* \* \*

UNITED STATES PATENT AND TRADEMARK OFFICE
CERTIFICATE OF CORRECTION

PATENT NO. : 7,632,385 B2
APPLICATION NO. : 11/162872
DATED : December 15, 2009
INVENTOR(S) : Philippe Ehrismann It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1114 days.

Signed and Sealed this

Second Day of November, 2010

David J. Kappos
*Director of the United States Patent and Trademark Office*